United States Patent
Harale et al.

(10) Patent No.: US 10,953,388 B1
(45) Date of Patent: *Mar. 23, 2021

(54) NI—RU—CGO BASED PRE-REFORMING CATALYST FOR LIQUID HYDROCARBONS

(71) Applicants: Saudi Arabian Oil Company, Dhahran (SA); Korea Advanced Institute of Science and Technology, Daejeon (KR)

(72) Inventors: Aadesh Harale, Dhahran (SA); Sai P. Katikaneni, Dhahran (SA); Joongmyeon Bae, Daejeon (KR); Youshan Ma, Dhahran (SA); Ahmed Al-Naimi, Dhahran (SA)

(73) Assignees: Saudi Arabian Oil Company; Korea Advanced Institute of Science and Technology

(*) Notice: Subject to any disclaimer, the term of this patent is extended or adjusted under 35 U.S.C. 154(b) by 0 days.

This patent is subject to a terminal disclaimer.

(21) Appl. No.: 16/729,188

(22) Filed: Dec. 27, 2019

(51) Int. Cl.
*C07C 4/06* (2006.01)
*B01J 23/83* (2006.01)
(Continued)

(52) U.S. Cl.
CPC ............ *B01J 23/894* (2013.01); *B01J 23/96* (2013.01); *B01J 35/026* (2013.01); *B01J 37/08* (2013.01); *B01J 37/18* (2013.01); *B01J 38/06* (2013.01); *B01J 38/10* (2013.01); *C01B 3/38* (2013.01); *C07C 4/06* (2013.01);
(Continued)

(58) Field of Classification Search
None
See application file for complete search history.

(56) References Cited

U.S. PATENT DOCUMENTS 6,238,816 B1 5/2001 Cable et al.
6,458,741 B1 10/2002 Roark et al.
(Continued)

FOREIGN PATENT DOCUMENTS

EP 2012381 A1 1/2009
EP 2031675 A1 3/2009

OTHER PUBLICATIONS

Choi et al., "Pre-reforming of higher hydrocarbons contained associated gas using a pressurized reactor with a Ni19.5—Ru0.05/CGO catalyst", Chemical Engineering Science, 168 (2017), pp. 15-22. (Year: 2017).*

(Continued)

*Primary Examiner* — Philip Y Louie
(74) *Attorney, Agent, or Firm* — Bracewell LLP; Constance R. Rhebergen

(57) ABSTRACT

A method for producing a methane-rich gas from a heavy hydrocarbon feed, the method comprising the steps of introducing the heavy hydrocarbon stream to a catalytic reactor, the catalytic reactor comprising an activated catalyst, the activated catalyst comprising 20 wt % of nickel, 70 wt % of a cerium oxide component, and 10 wt % of a gadolinium oxide component; applying the heavy hydrocarbon stream to the activated catalyst; and producing the methane-rich gas over the activated catalyst, wherein the methane-rich gas is selected from the group consisting of methane, carbon dioxide, carbon monoxide, hydrogen, and combinations of the same.

17 Claims, 5 Drawing Sheets

(51) Int. Cl.
*B01J 23/89* (2006.01)
*B01J 37/18* (2006.01)
*B01J 35/02* (2006.01)
*B01J 38/10* (2006.01)
*B01J 38/06* (2006.01)
*C01B 3/38* (2006.01)
*B01J 23/96* (2006.01)
*B01J 37/08* (2006.01)

(52) U.S. Cl.
CPC ......... *C01B 2203/0233* (2013.01); *C01B 2203/1058* (2013.01); *C01B 2203/1241* (2013.01); *C07C 2523/10* (2013.01); *C07C 2523/46* (2013.01); *C07C 2523/755* (2013.01)

(56) References Cited

U.S. PATENT DOCUMENTS

| | | | |
|---|---|---|---|
| 6,749,829 | B2 | 6/2004 | Briscoe |
| 7,067,453 | B1 | 6/2006 | Ming et al. |
| 7,168,265 | B2 | 1/2007 | Briscoe et al. |
| 7,452,619 | B2 | 11/2008 | Ahmed |
| 7,473,466 | B1 | 1/2009 | Muradov |
| 7,572,429 | B1 | 8/2009 | Neylon et al. |
| 7,829,602 | B2 | 11/2010 | Litt et al. |
| 7,901,565 | B2 | 3/2011 | Giroux et al. |
| 8,076,121 | B2 | 12/2011 | O'Rear |
| 8,123,826 | B2 | 2/2012 | Pham |
| 9,181,148 | B2 | 11/2015 | Katikaneni et al. |
| 2004/0163312 | A1* | 8/2004 | Bloomfield .......... B01J 19/0006 48/214 A |
| 2004/0245086 | A1 | 12/2004 | Steynberg et al. |
| 2008/0003461 | A1 | 1/2008 | Chellappa |
| 2008/0003466 | A1 | 1/2008 | Stevens et al. |
| 2008/0057359 | A1 | 3/2008 | Venkataraman et al. |
| 2008/0262110 | A1 | 10/2008 | Lomax et al. |
| 2009/0155644 | A1 | 6/2009 | Cui et al. |
| 2009/0305090 | A1 | 12/2009 | Chuang |
| 2010/0018349 | A1 | 7/2010 | Hoke et al. |
| 2011/0024687 | A1 | 2/2011 | White et al. |
| 2011/0065017 | A1 | 3/2011 | Ha |
| 2012/0003565 | A1 | 1/2012 | Son et al. |
| 2012/0015266 | A1 | 1/2012 | Melo Faus et al. |
| 2012/0024757 | A1 | 2/2012 | Xia et al. |
| 2012/0070367 | A1 | 3/2012 | Bittencourt |
| 2018/0200695 | A1* | 7/2018 | Katikaneni .......... B01J 23/83 |

OTHER PUBLICATIONS

Lee et al., "Ni—Me/Ce0.9Gd0.1O2-x (Me: Rh, Pt and Ru) catalysts for diesel pre-reforming", International Journal of Hydrogen Energy, 2015, pp. 3207-3216. (Year: 2015).*

Ta-Jen Huang et al, "A Comparison of Oxygen-vacancy Effect on Activity Behaviors of Carbon Dioxide and Steam Reforming of Methane over Supported Nickel Catalysts", Catalysis Letters 105, pp. 239-247(2005).

Fridriksson, "Study on Catalytic Reactions in Solid Oxide Fuel Cells with Comparison to Gas Phase Reactions in Internal Combustion Engines", 2008 TFRF05 Fuel Cell Technology, Dec. 3, 2009, 8 pages.

Song, "Fuel processing for low temperature and high temperature fuel cells", Catalyst Today 77 (2002), 33 pages.

Zha et al., "Ni—Ce0.9Gd0.1O1.95 anode for GDC electrolyte-based low-temperature SOFCs", Elsevier, 166 Solid State Ionics 241-250 (2004), 10 pages.

Kang et al., "Autothermal reforming study of diesel for fuel cell application", 159 J. of Power Sources 1283-1290 (2006), 8 pages.

Kang et al., The micro-reactor testing of catalysts and fuel delivery apparatuses for diesel authothermal reforming, Catalysis Today 136 (2008), pp. 249-257.

Lu et al., "Highly sulfur-tolerant Pt/Ce0.8Gd0.2O1.9 catalyst for steam reforming of liquid hydrocarbons in fuel cell applications", Elsevier, ScienceDirect, Journal of Catalysis 254, pp. 39-48 (2008).

Prasad et al., "Single step synthesis of nano-sized NiOCe0.75Zr0.25O2 composite powders by glycine nitrate process", 62 Materials Letters 587-590 (2008), 4 pages.

Prasad et al., Internal Steam Reforming of Methane over Ni-GDC Anode Particles Prepared by Glycine-nitrate-process for SOFC Applications, The 10th Asian Hydrogen Energy Conference "AHEC2009", Daegu, Korea, 2009, pp. 217-233.

D. Hari Prasad, "Effect of Nickel Nano-Particle Sintering on methane reforming activity of Ni-CGO cermet anodes for internal reforming SOFCs", 101 Applied Catalysis B: Environmental 531-539 (2011), 9 pages.

\* cited by examiner

NI—RU—CGO BASED PRE-REFORMING CATALYST FOR LIQUID HYDROCARBONS

TECHNICAL FIELD

Disclosed are compositions and methods related to catalyst formulations. Specifically, disclosed are compositions and methods for catalyst formulations to convert hydrocarbons to methane-rich gas.

BACKGROUND

Energy is a growing global business, with rapid increases expected in transportation fuel consumption and in electricity production. Recent improvements to existing technology have added significant value to marginal resources of competing fuels or through more efficient conversion of oil-based fuel sources (for example, hybrids and diesel engines). Renewed interest in non-oil based hydrogen technologies represents a challenge to oil producers. But also, an opportunity for developing competitive petroleum-based conversion approaches and petroleum-based fuels to take advantage of a possible emerging change in customer and consumer preferences for energy products.

A well-established process in the petroleum industry for the production of hydrogen is the steam reforming process. The steam reforming process uses a nickel-based catalyst, which is highly sensitive to deactivation by sulfur poisoning and coke deposition. However, conventional processes require high amounts of nickel in the catalyst and higher temperatures in the reactors.

SUMMARY

Disclosed are compositions and methods related to catalyst formulations. Specifically, disclosed are compositions and methods for catalyst formulations to convert hydrocarbons to methane-rich gas.

In a first aspect, a method for producing a methane-rich gas from a heavy hydrocarbon feed is provided. The method includes the steps of introducing the heavy hydrocarbon stream to a catalytic reactor, the catalytic reactor includes an activated catalyst, the activated includes catalyst includes: 20 wt % of nickel, 70 wt % of a cerium oxide component, and 10 wt % of a gadolinium oxide component, applying the heavy hydrocarbon stream to the activated catalyst, and producing the methane-rich gas over the activated catalyst, where the methane-rich gas is selected from the group consisting of methane, carbon dioxide, carbon monoxide, hydrogen, and combinations of the same.

In certain aspects, the heavy hydrocarbon stream is selected from the group consisting of heavy naphtha, liquid petroleum gas, kerosene, and combinations of the same. In certain aspects, the heavy hydrocarbon stream includes heavy naphtha. In certain aspects, a temperature in the catalytic reactor is in the range between 500° C. and 600° C. In certain aspects, a pressure in the catalytic reactor is in the range between 1 bar and 40 bar. In certain aspects, the method further includes preparing the activated catalyst, where preparing the activated catalyst includes the steps of adding stoichiometric amounts of Ce(NO3)3.6H2O, Gd(NO3)3.6H2O, and Ni (NO3)3.6H2O to de-ionized water to create a dissolved solution, adding glycine to the dissolved solution to create a glycine-dis solved solution, heating the glycine-dis solved solution such that excess water is evaporated, combustion is initiated, and a pre-catalyst catalyst powder is produced, calcining the pre-catalyst powder in air at 800° C. for 4 hours to produce a calcined catalyst powder, and reducing the calcined catalyst powder in a reducing gas at 500° C. for a period of 4 hours to produce the activated catalyst. The method further includes the step of shaping the activating catalyst into pellets. In certain aspects, the molar ratio of nitrate to glycine is 1:1.5. In certain aspects, the step of calcining the pre-catalyst powder includes increasing the temperature to 800° C. over a period of about 4 hours, and then maintaining the temperature at 800° C. for 4 hours. In certain aspects, the reducing gas includes 30 vol % hydrogen. In certain aspects, the reducing gas includes 70 vol % nitrogen. In certain aspects, the method further includes the steps of producing the methane-rich gas over the activated catalyst until coke formation on the activated catalyst forms a spent catalyst, treating the spent catalyst with a regenerating gas at a regeneration temperature at atmospheric pressure for a sufficient amount of time to remove coke formation on the catalyst. In certain aspects, the regenerating gas includes 30 vol % hydrogen. In certain aspects, the regenerating gas includes 45 vol % nitrogen. In certain aspects, regenerating gas includes 45 vol % water. In certain aspects, a conversion of heavy hydrocarbons to methane-rich gas is greater than 90%. In certain aspects, the method further includes the step of treating the methane-rich gas in a reformer unit to produce a hydrogen gas stream, where the reformer unit is selected from the group consisting of a conventional steam reformer, a membrane reformer, and combinations of the same, where the hydrogen gas stream includes hydrogen.

In a second aspect, a method for producing a methane-rich gas from a heavy hydrocarbon feed is provided. The method includes the steps of introducing the heavy hydrocarbon stream to a catalytic reactor, the catalytic reactor includes an activated catalyst, the activated includes catalyst includes: 19.5 wt % of nickel, 0.5 wt % ruthenium, 70 wt % of a cerium oxide component, and 10 wt % of a gadolinium oxide component, applying the heavy hydrocarbon stream to the activated catalyst, and producing the methane-rich gas over the activated catalyst, where the methane-rich gas includes methane.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

DETAILED DESCRIPTION

While the scope will be described with several embodiments, it is understood that one of ordinary skill in the relevant art will appreciate that many examples, variations and alterations to the apparatus and methods described here are within the scope. Accordingly, the embodiments described are set forth without any loss of generality, and without imposing limitations, on the embodiments. Those of skill in the art understand that the scope includes all possible combinations and uses of particular features described in the specification.

Described here are compositions and methods of catalyst formulations for use in converting heavy naphtha hydrocarbons to methane-rich gases. Advantageously, maximizing the conversion of heavy hydrocarbons to methane in the pre-forming stage can make the combination of pre-forming stage and steam reforming more energy efficient.

As used throughout, "in the absence" means the composition or method does not include, does not contain, is without.

As used throughout, "heavy naphtha" refers to a hydrocarbon stream containing carbons having a carbon number between 1 and 10 with a final boiling point of 205° C. A heavy naphtha contains paraffins, 1-paraffins, aromatics, naphthenes, and olefins. The paraffins can be present about 12.5 wt %, the 1-paraffins can be present at about 29 wt %, the aromatics can be present at about 11 wt %, the naphthenes can be present at about 41.5 wt %, and the olefins can be present at about 6 wt %.

As used throughout, "carbon number" refers to the number of carbon atoms of a compound.

As used throughout, "diesel" refers to a hydrocarbon stream containing carbons having a carbon number between 14 and 26 with a final point of 280° C. Diesel can contain about 43 wt % paraffins, about 42 wt % naphthenes, and about 15 wt % aromatics.

The catalyst compositions can include a metal component, a cerium oxide component, and a gadolinium oxide component.

Figure 1:
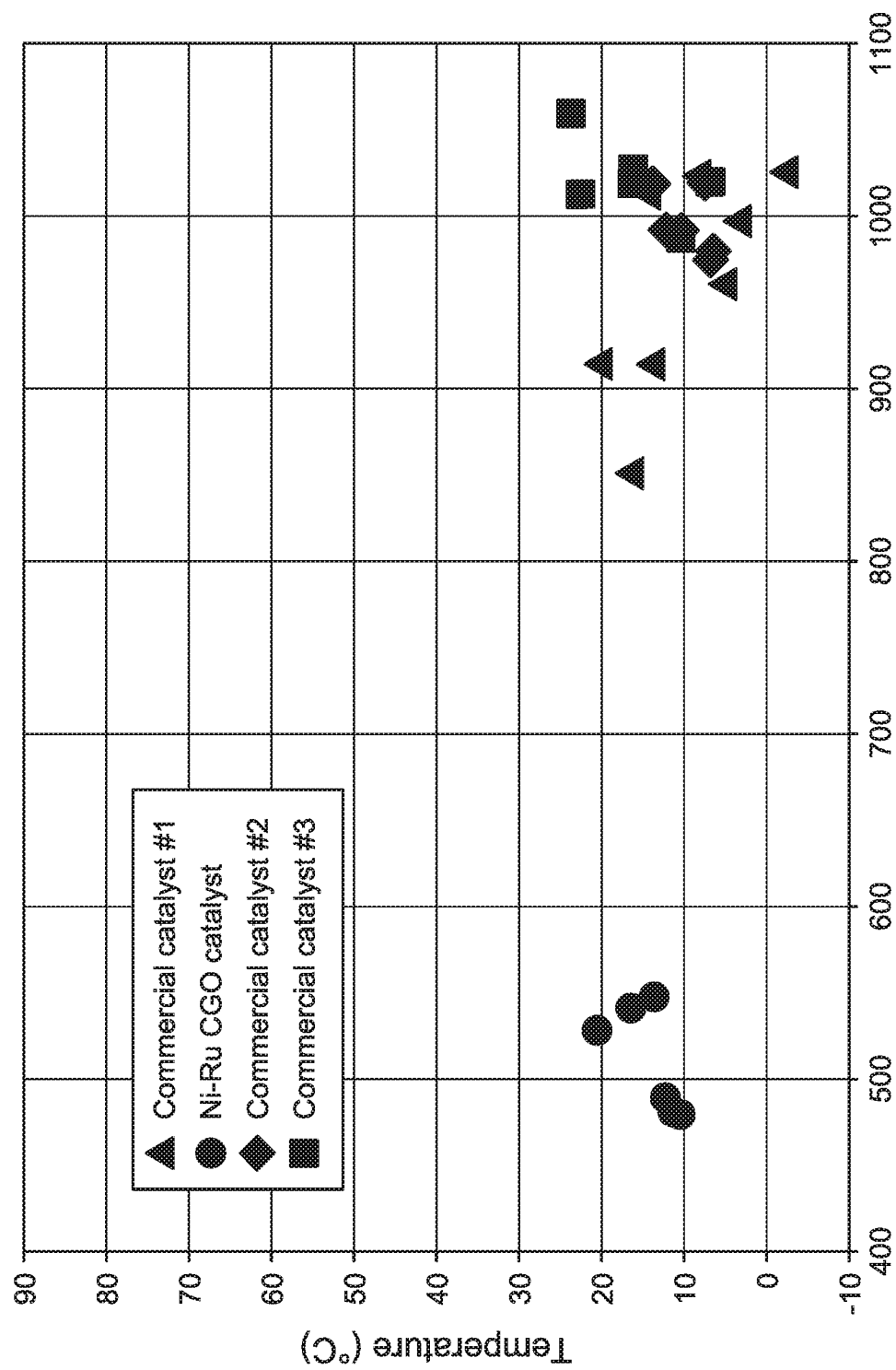
FIG. 1 provides a graph comparison of embodiments of the catalyst composition performance through approach to equilibrium criterion with commercial catalysts.

The metal component is present in an amount of 20 wt %. The metal component is an active metal of the catalyst. The metal component can include nickel and combinations of nickel and ruthenium. In at least one embodiment, the metal component includes nickel. The nickel can be present as nickel metal. The nickel is present at an amount of between about 20 percent by weight (wt %) and about 40 wt %, alternately about 20 wt %, and alternately about 19 wt %. In at least one embodiment, the metal component includes nickel and ruthenium. The nickel can be present as nickel metal and the ruthenium can be present as ruthenium metal. The nickel is present at an amount of about 19.5 wt % and the ruthenium is present at an amount of about 0.5 wt %. Advantageously, there is an optimum loading of nickel in the catalyst compositions. The optimum loading of nickel, at 20% wt, more effectively suppresses detrimental coke formation than higher nickel loadings, while maintaining high catalytic activity. Advantageously, the addition of a small amount of ruthenium improves the stability of the catalyst compositions. While nickel is widely used for catalytic processes because it has high catalytic activity and is inexpensive, nickel is vulnerable to coke formation compared to precious metals such as rhodium, platinum and ruthenium. FIG. 1 shows that a catalyst with 19.5 wt % nickel, 0.5 wt % ruthenium on a CGO catalyst support can perform at the same level as commercial catalysts, with amounts of nickel in the range between 40 wt % and 60 wt %, in the conversion of heavy naphtha to methane. Catalyst performance can be observed by measuring the temperature at the outlet of the catalyst bed, which can be indicative of whether the catalyst is achieving thermodynamic equilibrium.

The cerium oxide component can have the formula $CeO_2$. The cerium oxide component can be present in an amount of 70 wt %. The gadolinium oxide component can be present in an amount of 10 wt %. The cerium oxide component and gadolinium oxide component can be collectively referred to as "CGO" or "Gd doped $CeO_2$"). The CGO functions as the catalyst support. Advantageously, CGO is effective to improve the tolerance of the catalyst composition to coke formation and so suppresses coke formation on the catalyst. Without wishing to be bound by theory, it is believed that CGO suppresses coke formation on metals because CGO is an ionic conductive material. In some embodiments, the CGO has a high ionic conductivity.

In at least one embodiment, the catalyst composition includes a nickel component present at about 20 wt %, a cerium oxide component present at about 70 wt %, and a gadolinium oxide component present at about 10 wt %. In at least one embodiment, the catalyst composition includes a nickel component present at about 19.5 wt %, a ruthenium component present at about 0.5 wt %, a cerium oxide component present at about 70 wt %, and a gadolinium oxide component present at about 10 wt %.

The catalyst composition can be resistant to coke formation on the catalyst.

A method of preparing the catalyst composition for converting heavy hydrocarbons to a methane-rich gas using a glycine nitrate process ("GNP") is described. In a first step of the method, stoichiometric amounts of $Ce(NO3)3.6H_2O$, $Gd(NO3)3.6H_2O$ and $Ni(NO3)2.6H_2O$ are added to de-ionized water to create a dissolved solution. Glycine is added to the dissolved solution to create a glycine-dissolved solution. Glycine is used as a fuel in the GNP, and the glycine can be combusted. The molar ratio of nitrate to glycine in the dissolved solution can be 1:1.6, alternately 1:1.5 and alternately 1:1.4. The glycine can have a purity greater than or equal to 99%. The glycine-dissolved solution is heated to a temperature between 100° C. and 200° C. and alternately between 100° C. and 150° C. such that excess water is evaporated, combustion is initiated, and a pre-catalyst powder is produced. Evaporation of the water can take about 2 hours. Combustion can begin at about 180° C. and continue for between 10 minutes and 60 minutes.

The pre-catalyst powder is calcined in air at about 800° C. for a period of about 4 hours to produce a calcined catalyst powder. In at least one embodiment, the temperature of the pre-catalyst powder can be increased to about 800° C. over a period of about 4 hours and then the pre-catalyst powder can be calcined in air for a period of about 4 hours. The pre-catalyst powder is calcined in order to stabilize the active metal and form the phase of CGO ($Ce_{1-x}Gd_xO_{2-y}$), where x is between 0.1 and 0.3 and y is equal to x divided by 2 (y=x/2). Forming this phase of CGO during calcination is most effective to suppress coke formation.

The catalyst powder can be shaped into any form to produce a formed catalyst. The formed catalyst can have any form useful for converting heavy hydrocarbons to a methane-rich gas. In at least one embodiment, the catalyst powder is shaped into pellets. The pellets can be formed using a hydraulic press.

The size of the particles of the catalyst powder can be in the range between 10 nm and 20 nm and alternately between 250 microns and 500 microns.

The catalyst powder can be activated by reducing the catalyst powder with a reducing gas at about 500° C. for a period of about 4 hours to produce an activated catalyst. The reducing gas can include hydrogen, nitrogen, and combinations of the same. In at least one embodiment, the reducing gas contains about 30 percent of volume (vol %) hydrogen. In at least one embodiment, the reducing gas contains about 70 vol % nitrogen. The step of activating the catalyst powder can be performed on the formed catalyst. The step of activating the catalyst converts a non-active form of nickel oxide formed during the preparation of the catalyst composition to the active metal form of nickel.

The spent catalyst can be regenerated by treating the spent catalyst with a regenerating gas at a regeneration temperature for between 6 hours and 8 hours to remove coke formation on the catalyst. The regeneration temperature depends on the severity of coke formation on the catalyst with increased regeneration temperature used for increased severity of coke formation. The regeneration temperature can be in the range from about 500° C. to about 800° C. In at least one embodiment, the regeneration temperature is 500° C. In at least one embodiment, the coke formation is severe and the regeneration temperature is 800° C. The regenerating gas can include water, hydrogen, nitrogen and combinations of the same. In at least one embodiment, the regenerating gas contains 45 vol % water. In at least one embodiment, the regenerating gas contains 30 vol % hydrogen. In at least one embodiment, the regenerating gas contains 45 vol % nitrogen. During the regenerating step, about 90% of the coke formation on the catalyst can be removed, alternately greater than about 90% of the coke formation on the catalyst can be removed, alternately greater than about 92% of the coke formation on the catalyst can be removed, alternately greater than about 93% of the coke formation on the catalyst can be removed, alternately greater than about 94% of the coke formation on the catalyst can be removed, alternately greater than about 95% of the coke formation on the catalyst can be removed, alternately greater than about 96% of the coke formation on the catalyst can be removed, alternately greater than about 97% of the coke formation on the catalyst can be removed, alternately greater than about 98% of the coke formation on the catalyst can be removed, alternately greater than about 99% of the coke formation on the catalyst can be removed, and alternately 100% of the coke formation on the catalyst can be removed. The spent catalyst is produced by using the activated catalyst to convert heavy hydrocarbons to methane-rich gas.

The catalyst compositions described here can be used to convert heavy hydrocarbons to a methane-rich gas in a pre-forming stage. In the pre-reforming stage, a heavy hydrocarbon stream is introduced to a catalytic reactor. The heavy hydrocarbon stream can include heavy naphtha, liquid petroleum gas, kerosene, and combinations of the same. The heavy hydrocarbon stream is liquid. Advantageously, the catalyst compositions described here can be used across a variety of heavy hydrocarbons to produce methane-rich gas. In at least one embodiment, the heavy hydrocarbon stream includes heavy naphtha. The catalytic reactor can include the activated catalyst. The temperature in the catalytic reactor can be in the range between about 500° C. to about 600° C. The pressure in catalytic reactor can be in the range between 0 bar and 40 bar.

Figure 2:
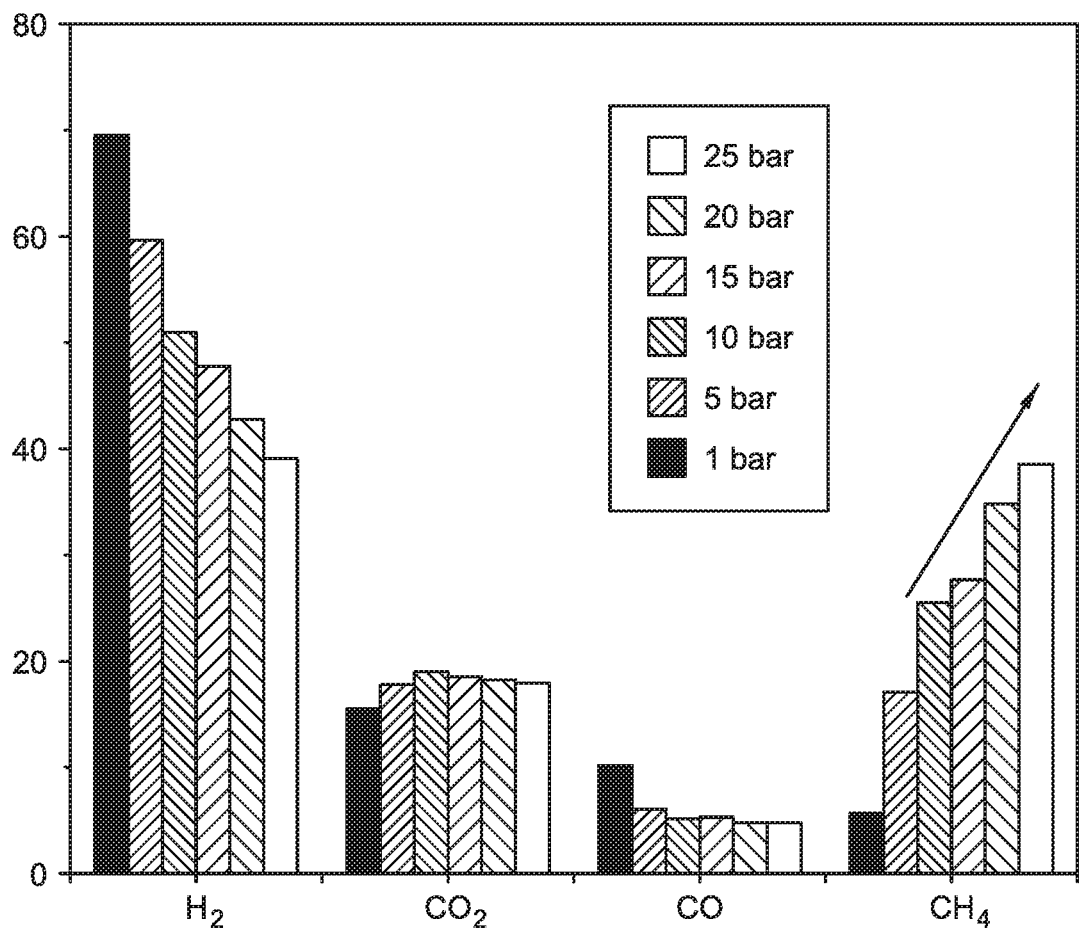
FIG. 2 shows the composition of methane-rich gas at various pressures at 550° C.

As can be seen in FIG. 2, in a process to convert heavy naphtha to a methane-rich gas stream, the amount of methane produced increases as the pressure in catalytic reactor increases at a constant temperature of 550° C. The temperature and pressure in the catalytic reactor can be selected such that the catalytic reactor operates adiabatically such that external energy is not required to maintain the reaction conditions. The steam reforming reaction is endothermic and the methanation reaction, which produces methane from hydrogen and carbon dioxide, is exothermic, thus the operating conditions can be selected to balance the energy produced in each of these reactions to produce adiabatic conditions.

The heavy hydrocarbon stream is applied to the activated catalyst to produce the methane-rich gas. The methane-rich gas contains methane, carbon dioxide, carbon monoxide, hydrogen, and combinations of the same.

The conversion of heavy hydrocarbons to methane-rich gas can be greater than 50%, alternately greater than 60%, alternately greater than 70%, alternately greater than 80%, and alternately greater than 90%. The conversion of heavy hydrocarbons to methane can be greater than 50%, alternately greater than 60%, and alternately greater than 70% with the remaining gas in the methane-rich gas including carbon dioxide, carbon monoxide, and hydrogen.

The methane-rich gas stream can be further treated in a reformer unit to produce a hydrogen gas stream. The reformer unit can include a conventional steam reformer, a membrane reformer, and combinations of the same. The conventional steam reformer can include a convention reactor, a membrane reactor, or combinations of the same. The conventional steam reformer can operate at pressures in the range between 10 bar and 40 bar and temperatures in the range between 800° C. and 900° C. A membrane reformer includes a hydrogen selective membrane integrated with steam reforming catalyst, such that the membrane removes hydrogen produced when methane contacts the steam reforming catalyst. Removing hydrogen from the reaction environment results in a higher conversion in the membrane reformer than thermodynamic equilibrium suggests. Separating hydrogen and carbon dioxide during the reaction achieves near complete conversions. The membrane reformer can operate at pressures in the range between 10 bar and 40 bar and temperatures in the range between 450° C. and 600° C. The hydrogen gas stream can include hydrogen. Advantageously, the use of the catalytic reactor upstream of the reformer unit results in a method to produce hydrogen gas that has increased efficiency due to the operating conditions of the catalytic reactor. Advantageously, the use of the catalytic reactor upstream of the reformer unit provides greater flexibility in the feedstock that be utilized to produce hydrogen.

Figure 3:
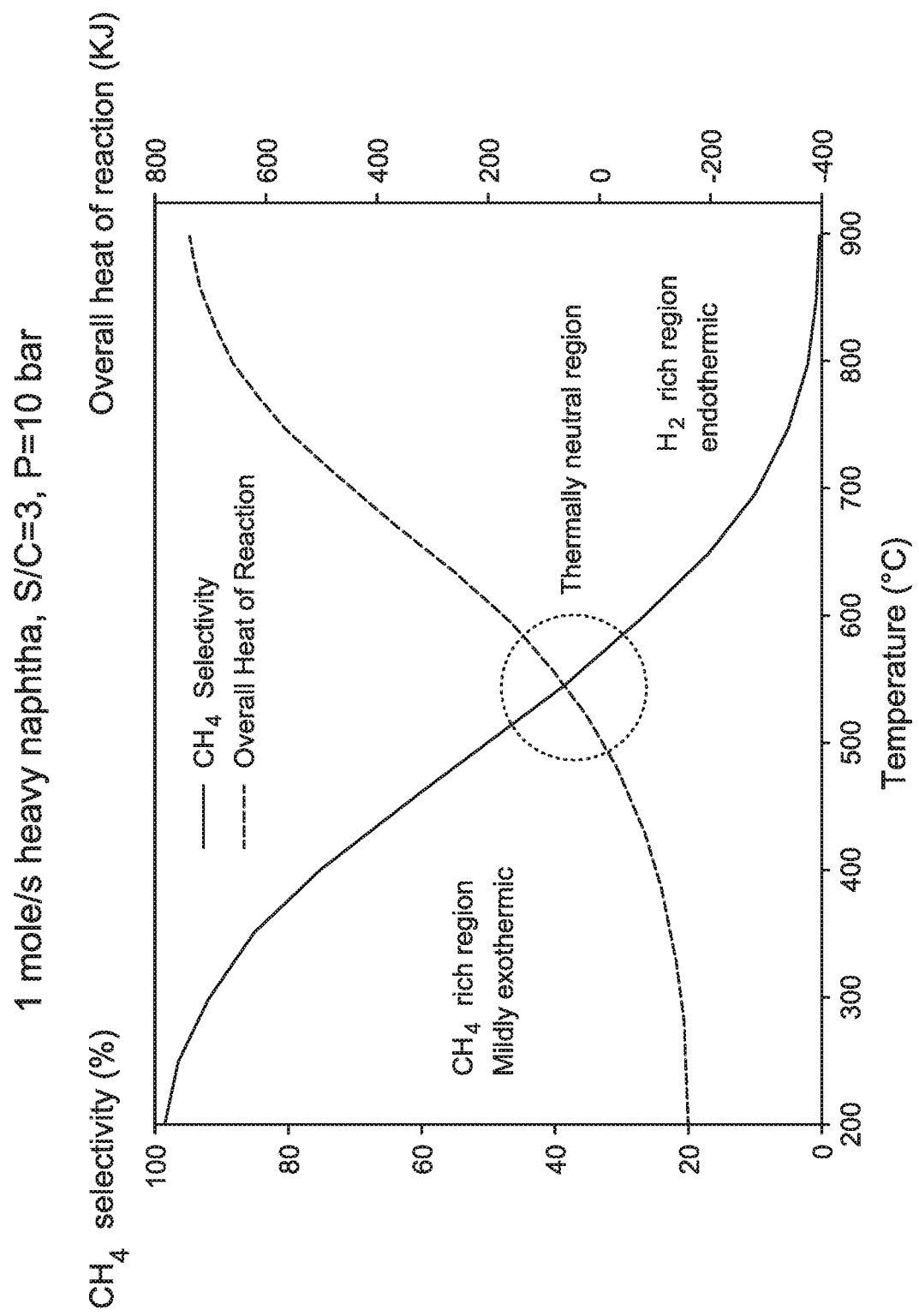
FIG. 3 shows the target region to have thermal neutrality and a methane-rich product stream.

FIG. 3 shows the operating regions of stream reforming in the temperature range from 200° C. to 900° C. The lower temperatures, in the range between 200° C. and 550° C., and higher temperatures, in the range between 800° C. and 900° C. are the hydrogen rich regions in a steam reforming process, where syngas is formed and then subsequently shifted through water-gas shift reaction to produce hydrogen. The right hand y-axis shows the heat of reaction and as can be seen the region between 500° C. and 600° C. is a thermally neutral region, where the reaction can be sustained without external energy inputs.

The pre-forming stage and reformer unit can be combined to produce hydrogen fuel for transportation vehicles. The pre-forming stage and reformer unit can be combined for a hydrogen fueling station in any applications requiring a hydrogen feed stream. Such applications can include refinery applications, glass factory, food industry, metal industry. The pre-forming stage and reformer unit can be combined in a fuel cell for power generation.

The catalyst composition is in the absence of platinum. The methods for producing a methane-rich gas stream are in the absence of oxygen in the reactor feed. The heavy hydrocarbon stream is in the absence of diesel.

EXAMPLES

Figure 4:
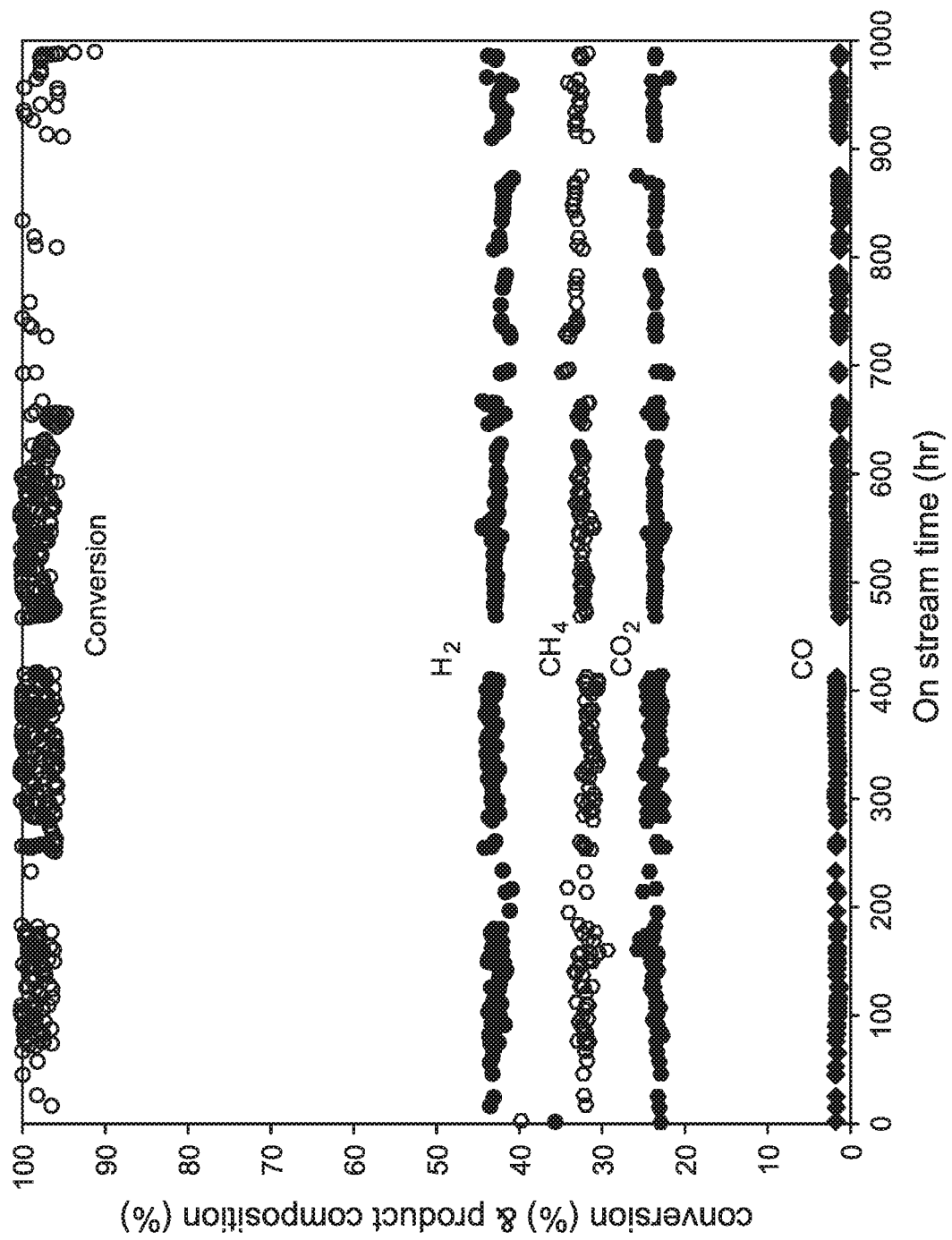
FIG. 4 shows the composition of the methane-rich gas stream from Example 1.

Example 1. In Example 1, a long-term stability test of the catalyst composition was performed. A catalyst composition of 20 wt % nickel, 70 wt % cerium oxide component, and 10 wt % gadolinium oxide component was prepared. The heavy hydrocarbon stream was a heavy naphtha. The test was conducted at a molar ratio of steam to carbon of 3.5 $H_2O/C$, at a temperature of 550° C. and a pressure of 25 bar for 1,000 hours. A continuous stream of a methane-rich gas was produced. The methane-rich gas stream contained 32 mol % methane and was in the absence of water and nitrogen. The methane-rich gas stream had a consistent composition across the 1,000 hour test run as can be seen in FIG. 4.

Figure 5:
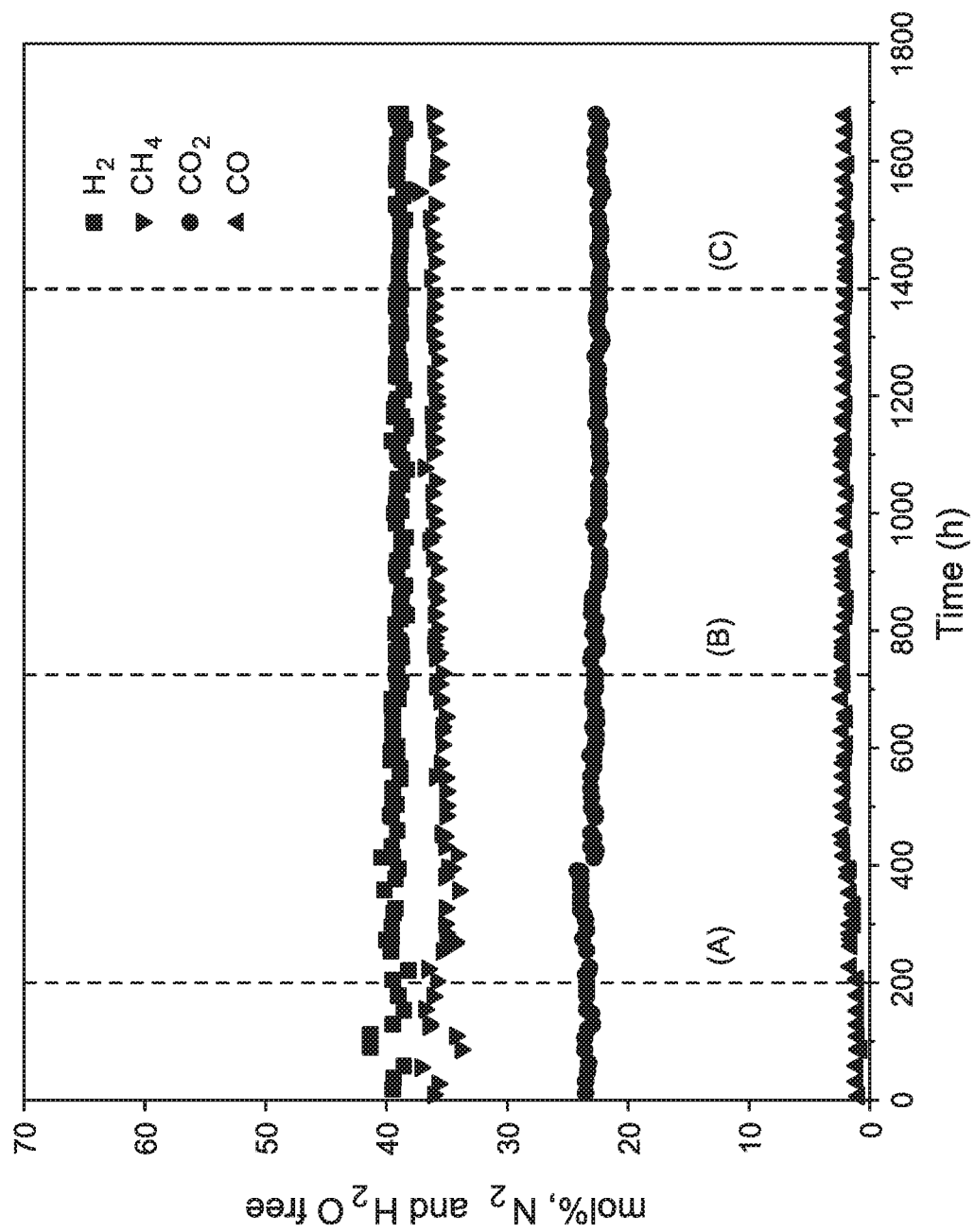
FIG. 5 shows the composition of the methane-rich gas stream from Example 2.

Example 2. In Example 2, a catalyst composition of 19.5 wt % nickel, 0.5 wt % ruthenium, 70 wt % cerium oxide component, and 10 wt % gadolinium oxide component was prepared. The heavy hydrocarbon stream was a heavy naphtha. The test was conducted at a flow rate of 3.0 liter/hour, a temperature of 565° C., and a pressure of 25 bar for 1,600 hours. A continuous stream of a methane-rich gas was produced. The methane-rich gas stream contained about 36 mol % methane and was in the absence of water and nitrogen. The methane-rich gas stream had a consistent composition across the 1,600 hour test run as can be seen in FIG. 5.

Examples 1 and 2 exhibit stable catalyst performance.

Although the embodiments here have been described in detail, it should be understood that various changes, substitutions, and alterations can be made hereupon without departing from the principle and scope of the embodiments. Accordingly, the scope should be determined by the following claims and their appropriate legal equivalents.

There various elements described can be used in combination with all other elements described here unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed here as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the embodiments pertain, except when these references contradict the statements made here.

As used here and in the appended claims, the words "comprise," "has," and "include" and all grammatical variations of the same are each intended to have an open, non-limiting meaning that does not exclude additional elements or steps.

As used here, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present embodiments.

That which is claimed is:

1. A method for producing a methane-rich gas from a heavy hydrocarbon stream, the method comprising the steps of:
   introducing the heavy hydrocarbon stream to a catalytic reactor, wherein the heavy hydrocarbon stream is selected from the group consisting of heavy naphtha, kerosene, and combinations of the same, wherein the heavy hydrocarbon stream is in the absence of diesel, and wherein the heavy naphtha comprises paraffins, 1-paraffins, aromatics, naphthenes, and olefins, the catalytic reactor comprising an activated catalyst, the activated catalyst comprising:
   20 wt % of nickel,
   70 wt % of a cerium oxide component, and
   10 wt % of a gadolinium oxide component;
   applying the heavy hydrocarbon stream to the activated catalyst;
   operating the catalytic reactor at a temperature and pressure such that the catalytic reactor operates adiabatically, wherein the pressure in the catalytic reactor is between 11 bar and 40 bar; and
   producing the methane-rich gas over the activated catalyst, wherein the methane-rich gas comprises methane and further comprises at least one gas selected from the group consisting of carbon dioxide, carbon monoxide, hydrogen, and combinations of the same.

2. The method of claim 1, wherein the heavy hydrocarbon stream is heavy naphtha.

3. The method of claim 1, wherein a temperature in the catalytic reactor is in the range between 500° C. and 600° C.

4. The method of claim 1, further comprising preparing the activated catalyst, where preparing the activated catalyst comprises the steps of:
   adding stoichiometric amounts of $Ce(NO_3)_3 \cdot 6H_2O$, $Gd(NO_3)_3 \cdot 6H_2O$, and $Ni(NO_3)_3 \cdot 6H_2O$ to de-ionized water to create a dissolved solution;
   adding glycine to the dissolved solution to create a glycine-dissolved solution;
   heating the glycine-dissolved solution such that excess water is evaporated, combustion is initiated, and a pre-catalyst powder is produced;
   calcining the pre-catalyst powder in air at 800° C. for 4 hours to produce a calcined catalyst powder; and
   reducing the calcined catalyst powder in a reducing gas at 500° C. for a period of 4 hours to produce the activated catalyst.

5. The method of claim 4, further comprising a step of shaping the activating catalyst into pellets.

6. The method of claim 4, wherein a molar ratio of nitrate to glycine is 1:1.5.

7. The method of claim 4, wherein the step of calcining the pre-catalyst powder comprises increasing the temperature to 800° C. over a period of about 4 hours, and then maintaining the temperature at 800° C. for 4 hours.

8. The method of claim 4, wherein the reducing gas comprises 30 vol % hydrogen.

9. The method of claim 4, wherein the reducing gas comprises 70 vol % nitrogen.

10. The method of claim 1, further comprising the steps of:
    producing the methane-rich gas over the activated catalyst until coke formation on the activated catalyst forms a spent catalyst; and
    treating the spent catalyst with a regenerating gas at a regeneration temperature at atmospheric pressure for a sufficient amount of time to remove coke formation on the catalyst.

11. The method of claim 10, wherein the regenerating gas comprises 30 vol % hydrogen.

12. The method of claim 10, wherein the regenerating gas comprises 45 vol % nitrogen.

13. The method of claim 10, wherein regenerating gas comprises 45 vol % water.

14. The method of claim 1, wherein a conversion of heavy hydrocarbons to methane-rich gas is greater than 90%.

15. The method of claim 1, further comprising the step of treating the methane-rich gas in a reformer unit to produce a hydrogen gas stream, wherein the reformer unit is selected from the group consisting of a conventional steam reformer, a membrane reformer, and combinations of the same, wherein the hydrogen gas stream comprises hydrogen.

16. A method for producing a methane-rich gas from a heavy hydrocarbon stream, the method comprising the steps of:
introducing the heavy hydrocarbon stream to a catalytic reactor, wherein the heavy hydrocarbon stream is selected from the group consisting of heavy naphtha, kerosene, and combinations of the same, wherein the heavy hydrocarbon stream is in the absence of diesel, wherein the heavy naphtha comprises paraffins, 1-paraffins, aromatics, naphthenes, and olefins, the catalytic reactor comprising an activated catalyst, the activated catalyst comprising:
19.5 wt % of nickel,
0.5 wt % ruthenium,
70 wt % of a cerium oxide component, and
10 wt % of a gadolinium oxide component;
applying the heavy hydrocarbon stream to the activated catalyst;
operating the catalytic reactor at a temperature and pressure such that the catalytic reactor operates adiabatically, wherein the pressure in the catalytic reactor is between 11 bar and 40 bar; and
producing the methane-rich gas over the activated catalyst, wherein the methane-rich gas comprises methane.

17. The method of claim 16, wherein a temperature in the catalytic reactor is in the range between 500° C. and 600° C.

\* \* \* \* \*